(12) United States Patent
Tabandeh et al.

(10) Patent No.: US 12,329,470 B2
(45) Date of Patent: Jun. 17, 2025

(54) SYSTEM AND METHOD FOR AUTOMATED DOCKING

(71) Applicant: INTUITIVE SURGICAL OPERATIONS, INC., Sunnyvale, CA (US)

(72) Inventors: Saleh Tabandeh, Santa Clara, CA (US); Daniel H. Gomez, Los Gatos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 873 days.

(21) Appl. No.: 17/422,697

(22) PCT Filed: Jan. 13, 2020

(86) PCT No.: PCT/US2020/013395
§ 371 (c)(1),
(2) Date: Jul. 13, 2021

(87) PCT Pub. No.: WO2020/150165
PCT Pub. Date: Jul. 23, 2020

(65) Prior Publication Data
US 2022/0117680 A1    Apr. 21, 2022

Related U.S. Application Data

(60) Provisional application No. 62/792,162, filed on Jan. 14, 2019.

(51) Int. Cl.
*A61B 34/00*    (2016.01)
*A61B 34/20*    (2016.01)
(Continued)

(52) U.S. Cl.
CPC .............. *A61B 34/30* (2016.02); *A61B 34/20* (2016.02); *A61B 34/32* (2016.02); *A61B 90/08* (2016.02);
(Continued)

(58) Field of Classification Search
CPC ......... A61B 34/30; A61B 34/20; A61B 34/32; A61B 90/08; A61B 90/361; A61B 90/50;
(Continued)

(56) References Cited

U.S. PATENT DOCUMENTS 10,136,956 B2    11/2018    Seeber
11,911,910 B2 *    2/2024    Gonenc .................. A61B 34/37
(Continued)

FOREIGN PATENT DOCUMENTS

WO    WO-2015142812 A1    9/2015
WO    WO-2018217431 A1    11/2018

OTHER PUBLICATIONS

International Search Report and Written Opinion for Application No. PCT/US2020/013395, mailed Apr. 28, 2020, 11 pages.
(Continued)

*Primary Examiner* — Ian Jen
(74) *Attorney, Agent, or Firm* — Artegis Law Group, LLP

(57) ABSTRACT

Systems and methods for automated docking include a linkage, a docking arm located near a distal end of the linkage, a docking support mechanism, and one or more processors. The one or more processors are configured to detect a docking port using the docking support mechanism and actuate the linkage based on the detection to align the docking arm with the docking port, move the docking arm toward the docking port, and dock the docking arm to the docking port. In some embodiments, to actuate the linkage based on the detection, the one or more processors are configured to align the docking arm with an alignment point (Continued)

of the docking port, align an alignment axis of the docking arm with an alignment axis of the docking port, rotationally align the docking arm with the docking port, and reduce a relative distance between the docking arm and the docking port.

20 Claims, 6 Drawing Sheets

(51) Int. Cl.
    *A61B 34/30*     (2016.01)
    *A61B 34/32*     (2016.01)
    *A61B 90/00*     (2016.01)
    *A61B 90/50*     (2016.01)

(52) U.S. Cl.
    CPC ............ *A61B 90/361* (2016.02); *A61B 90/50* (2016.02); *A61B 2090/0808* (2016.02); *A61B 2090/3983* (2016.02)

(58) Field of Classification Search
    CPC .... A61B 2090/0808; A61B 2090/3983; A61B 2034/2051; A61B 17/34; A61B 2017/00477; A61B 2017/00482; A61B 2017/347; A61B 2034/2048; A61B 2034/2055; A61B 2034/2061; A61B 2034/2065

See application file for complete search history.

(56) References Cited

U.S. PATENT DOCUMENTS

| | | | |
|---|---|---|---|
| 2017/0000575 A1* | 1/2017 | Griffiths | A61B 50/10 |
| 2017/0065364 A1* | 3/2017 | Schuh | A61B 46/00 |
| 2017/0105811 A1* | 4/2017 | Garbus | A61B 17/3476 |
| 2017/0172674 A1* | 6/2017 | Hanuschik | A61B 34/30 |
| 2018/0049824 A1 | 2/2018 | Harris et al. | |
| 2018/0177523 A1 | 6/2018 | Piron et al. | |
| 2019/0029766 A1* | 1/2019 | Griffiths | A61B 34/25 |
| 2019/0380801 A1* | 12/2019 | Savall | A61B 34/74 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2020/013395, mailed on Jul. 29, 2021, 8 pages.

* cited by examiner

SYSTEM AND METHOD FOR AUTOMATED DOCKING

CROSS-REFERENCE TO RELATED APPLICATIONS

This application a U.S. National Stage patent application of International Patent Application No. PCT/US2020/013395, filed Jan. 13, 2020, the benefit of which is claimed, and claims the benefit of U.S. Provisional Application 62/792,162 filed Jan. 14, 2019, each of which is incorporated by reference herein in its entirety.

TECHNICAL FIELD

The present disclosure relates generally to operation of devices with end effectors and more particularly to operation of the devices to automatically dock them to a docking port.

BACKGROUND

More and more devices are being replaced with computer-assisted electronic devices. This is especially true in industrial, entertainment, educational, and other settings. As a medical example, the hospitals of today with large arrays of electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical and other medical tools are being replaced by computer-assisted medical devices.

These computer-assisted devices are useful for performing operations and/or procedures on materials, such as the tissue of a patient. Before many of these computer-assisted devices may be used to perform the procedure on the material, they are moved into position where that the end effectors may be used to reach the material of interest so that the procedure may be performed. In many instances, access to the material of interest is constrained to occur through an access port giving access to a workspace containing the material of interest. As a medical example, the access port may be a hollow cannula or trocar that is inserted through an incision in the patient and through which a shaft of one or more tools is inserted. As a non-medical example, the access port may be a valve opening into the workspace that the shaft of one or more tools is inserted and which helps isolate the workspace from outside contamination.

In order for the access port to be used, the one or more tools are positioned and aligned to pass through the access port. This typically requires that portions of the computer-assisted device, which are proximal to the one or more tools, be maneuvered into proper position and orientation relative to the access port. This is sometimes includes docking the computer-assisted device to a docking port of the access port. In many instances, this is not a trivial task.

Accordingly, improved methods and systems for the operation of computer-assisted devices that help position and orient one or more tools relative to an access port are desirable. In some examples, the improved methods and systems may include docking a computer-assisted device to a docking port.

SUMMARY

Consistent with some embodiments, a computer-assisted device includes a linkage, a docking arm located near a distal end of the linkage, a docking support mechanism, and one or more processors coupled to the linkage and the docking support mechanism. The one or more processors are configured to detect a docking port using the docking support mechanism and actuate the linkage based on the detection to align the docking arm with the docking port, move the docking arm toward the docking port, and dock the docking arm to the docking port.

Consistent with some embodiments, a method includes detecting, by one or more processors, a docking port using a docking support mechanism and actuating, by the one or more processors, a linkage of a docking arm of a computer-assisted device based on the detecting. The actuating includes aligning the docking arm with the docking port, moving the docking arm toward the docking port, and docking the docking arm with the docking port.

Consistent with some embodiments, a non-transitory machine-readable medium including a plurality of machine-readable instructions which when executed by one or more processors are adapted to cause the one or more processors to perform any of the methods described herein.

Figure 1:
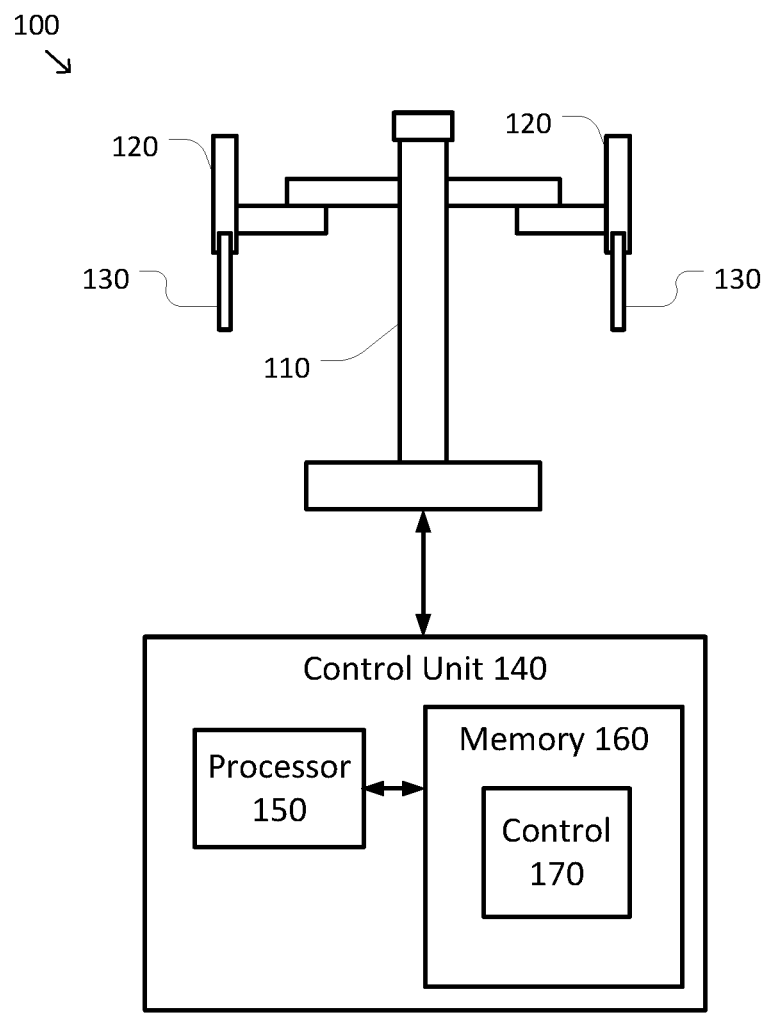
FIG. 1 is a simplified diagram of a computer-assisted system according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like-may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, the term "shape" refers to a set positions or orientations measured along an element. As used herein, and for a device with repositionable arms, the term "proximal" refers to a direction toward the base of the computer-assisted device along its kinematic chain and "distal" refers to a direction away from the base along the kinematic chain.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on da Vinci® Surgical Systems are merely exemplary and are not to be considered as limiting the scope of the inventive aspects disclosed herein. For example, techniques described with reference to surgical tools and surgical methods may be used in other contexts. Thus, the tools, systems, and methods described herein may be used for humans, animals, portions of human or animal anatomy, industrial systems, general robotic, or teleoperational systems. As further examples, the tools, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

FIG. 1 is a simplified diagram of a computer-assisted system 100 according to some embodiments. As shown in FIG. 1, computer-assisted system 100 includes a device 110 with one or more repositionable arms 120. Each of the one or more repositionable arms 120 may support one or more tools 130. In some examples, device 110 may be consistent with a computer-assisted medical device. The one or more tools 130 may include tools, imaging devices, and/or the like. In some medical examples, the tools may include medical tools, such as clamps, grippers, retractors, cautery tools, suction tools, suturing devices, and/or the like. In some medical examples, the imaging devices may include endoscopes, cameras, ultrasonic devices, fluoroscopic devices, and/or the like. In some examples, each of the one or more tools 130 may be inserted into a workspace (e.g., anatomy of a patient, a veterinary subject, and/or the like) through a respective cannula docked to a respective one of the one or more repositionable arms 120. In some examples, a direction of view of an imaging device may correspond to an insertion axis of the imaging device and/or may be at an angle relative to the insertion axis of the imaging device. In some examples, each of the one or more tools 130 may include an end effector that may be capable of both grasping a material (e.g., tissue of a patient) located in the workspace and delivering energy to the grasped material. In some examples, the energy may include ultrasonic, radio frequency, electrical, magnetic, thermal, light, and/or the like. In some embodiments, computer-assisted system 100 may be found in an operating room and/or an interventional suite.

Device 110 is coupled to a control unit 140 via an interface. The interface may include one or more cables, connectors, and/or buses and may further include one or more networks with one or more network switching and/or routing devices. Control unit 140 includes a processor 150 coupled to memory 160. Operation of control unit 140 is controlled by processor 150. And although control unit 140 is shown with only one processor 150, it is understood that processor 150 may be representative of one or more central processing units, multi-core processors, microprocessors, microcontrollers, digital signal processors, field programmable gate arrays (FPGAs), application specific integrated circuits (ASICs), graphics processing units (GPUs), tensor processing units (TPUs), and/or the like in control unit 140. Control unit 140 may be implemented as a stand-alone subsystem and/or as a board added to a computing device or as a virtual machine.

Memory 160 may be used to store software executed by control unit 140 and/or one or more data structures used during operation of control unit 140. Memory 160 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 160 includes a control module 170 that is responsible for controlling one or more aspects of the operation of computer-assisted device 110 so that one or more of the repositionable arms may be docked to a docking port. In some examples, the docking may include one or more of detecting the docketing port, determining a relative position between a docking arm on one of the repositionable arms 120 and the docking port, docking the docking arm with the docking port, and confirming the docking as is described in further detail below. And although control module 170 is characterized as a software module, control module 170 may be implemented using software, hardware, and/or a combination of hardware and software.

As discussed above and further emphasized here, FIG. 1 is merely an example which should not unduly limit the scope of the claims. One of ordinary skill in the art would recognize many variations, alternatives, and modifications. According to some embodiments, computer-assisted system 100 may include any number of computer-assisted devices with articulated arms and/or tools of similar and/or different in design from computer-assisted device 110. In some examples, each of the computer-assisted devices may include fewer or more articulated arms and/or tools.

Figure 2:
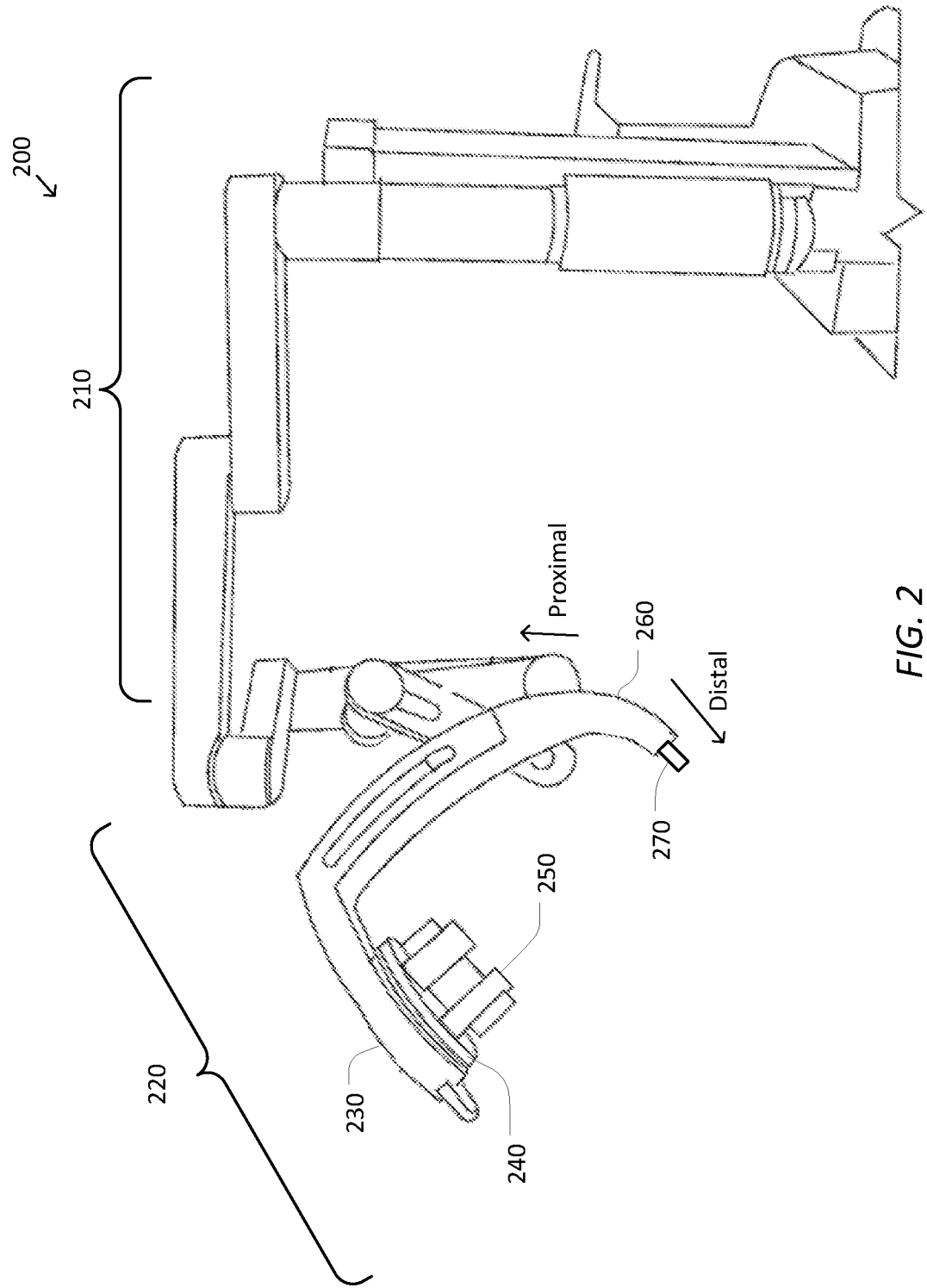
FIG. 2 is a simplified diagram of a computer-assisted device according to some embodiments.

FIG. 2 is a simplified diagram of a computer-assisted device 200 according to some embodiments. In some embodiments, computer-assisted device 200 may be consistent with computer-assisted device 110. As shown in FIG. 2, computer-assisted device 200 includes a support structure 210 used to support a manipulator assembly 220. Manipulator assembly 220 includes an entry guide platform 230 supporting an entry guide assembly 240 having a plurality of tool manipulators 250. Each of the tool manipulators 250 may have a corresponding tool (not shown) mounted to them that are to be inserted into a workspace through an access port (not shown).

Manipulator assembly 220 further includes a mounting linkage 260 that, near its distal end, supports a docking arm 270 that may be docked to a docking port (not shown) of the access port. In some examples, docking arm 270 may be fixed relative to mounting linkage 260 and/or may telescope in and out of the distal end of mounting linkage 260. Examples of telescoping docking arms are described in further detail in commonly-owned International Patent Application Publication WO2017/120027 A1, which is incorporated by reference herein.

According to some embodiments, it may not be practical for an operator to perform the docking between docking arm 270 and the docking port of the access port without assistance. In some examples, having an operator steer docking arm 270 into position for docking with the docking port (e.g., teleoperatively) may be tedious and/or time-consuming. In some examples, having an operator manually move the docking arm 270 into position for docking using a clutched mode of computer-assisted device 200 where manual repositioning of manipulator assembly 220 and/or mounting linkage 260 is permitted may not be practical because the large mass of manipulator assembly 220 and/or mounting linkage 260 may require the operator to exert large forces on mounting linkage 260 that would make the fine motions involved in aligning and/or orienting mounting arm 260 with the docking port difficult at best. Accordingly, automated and/or semi-automated mechanisms for performing the docking between mounting arm 270 and the docking port, where movement of mounting arm 270 is performed using one or more actuators of computer-assisted device 200 would be useful.

Figure 3A:
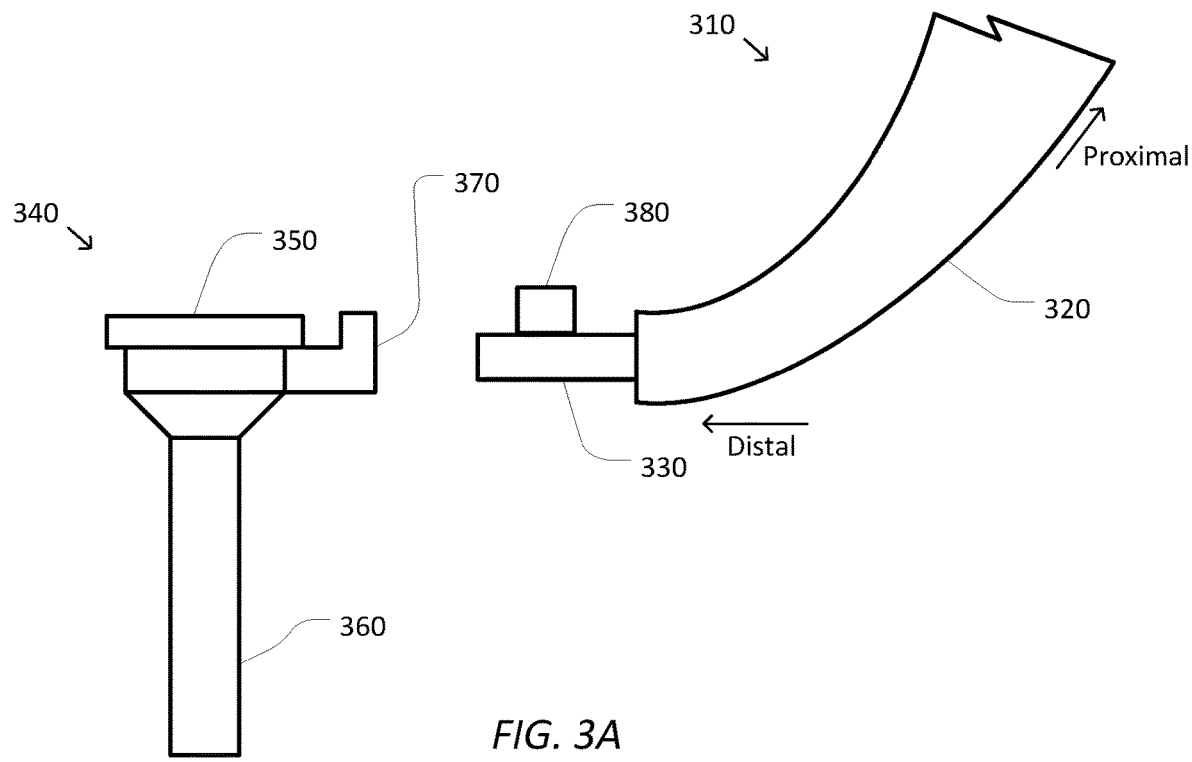
FIGS. 3A and 3B are simplified side views of a distal end of a computer-assisted device approaching a docking port according to some embodiments.
Figure 3B:
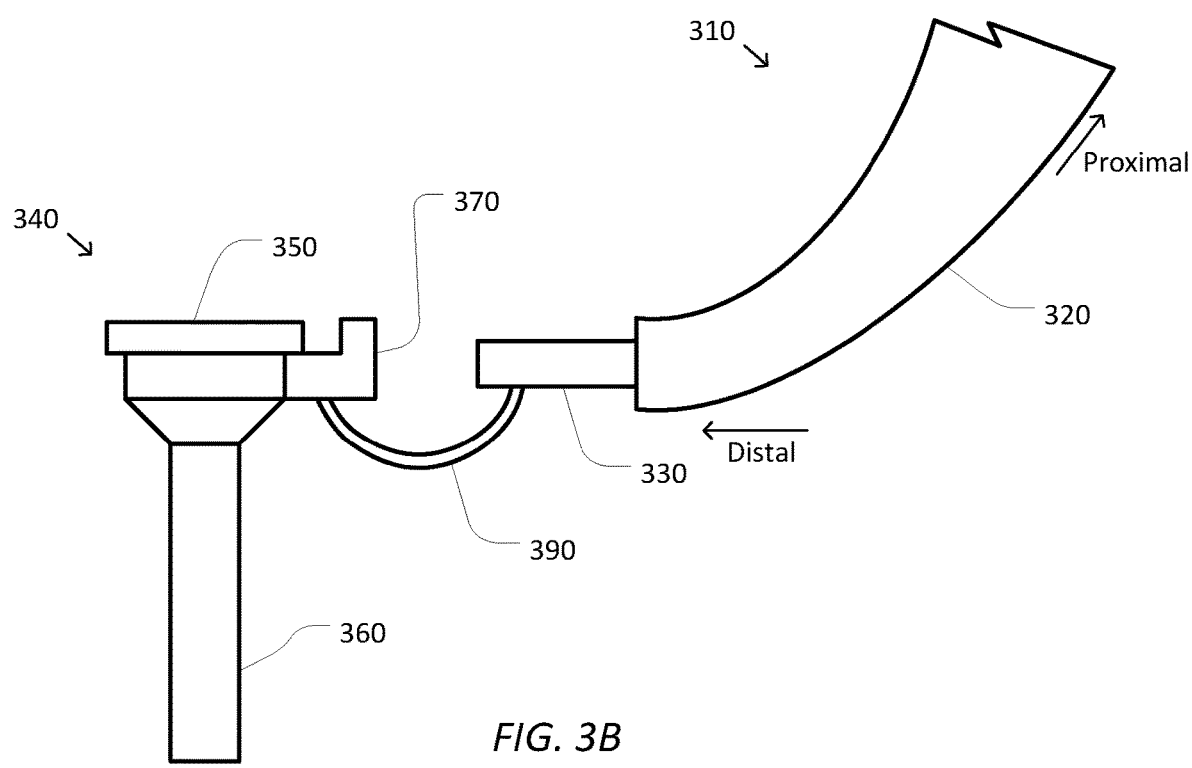

FIGS. 3A and 3B are simplified side views of a distal end of a computer-assisted device 310 approaching a docking port 340 according to some embodiments. In some embodiments, computer-assisted device 310 may be consistent with computer-assisted device 200 and/or 110. As shown in FIGS. 3A and 3B, computer-assisted device 310 includes a mounting linkage 320 that, near its distal end, supports a docking arm 330. In some embodiments mounting linkage 320 may be consistent with mounting linkage 260 and/or docking arm 330 may be consistent with docking arm 270.

As further shown in FIGS. 3A and 3B, access port 340 includes an aperture 350 providing access to a hollow tube 360. In some examples, aperture 350 and hollow tube 360 are configured to allow one or more tools to be inserted through aperture 350 and hollow tube 360 in order to provide access to a workspace for the one or more tools. Access port 340 further includes a docking port 370 that is configured to be docked with docking arm 330 as is described in further detail below. In some medical examples, access port 340 may be consistent with a cannula and/or a trocar and may provide the one or more tools access to interior anatomy of a patient. Examples of cannulas suitable for use with a docking arm are described in more detail in commonly-owned International Patent Publication No. WO2015US20916, which is incorporated by reference herein.

In order to help automate the docking of docking arm 330 to docking port 370, computer-assisted device 310 includes one or more docking support mechanisms to facilitate the detection of docking port 370, determining a relative position and/or orientation of docking arm 330 to docking port 370, and detecting successful docking between docking arm 330 and docking port 370. FIGS. 3A and 3B show examples of different embodiments of docking support mechanisms.

As shown in FIG. 3A, the one or more docking support mechanisms include an imaging device 380 mounted on docking arm 330. And although imaging device 380 is shown mounted on docking arm 330, imaging device 380 may be located in other locations, such as near the distal end of mounting linkage 320. As shown, imaging device 380 is mounted so that it provides one or more images distal to mounting arm 320. In some examples, the one or more images show access port 340 and/or docking port 370 as seen by docking arm 330. In some examples, the one or more images may be analyzed by computer-assisted device 310 and/or a computer-assisted system coupled with computer-assisted device 310 (e.g., control unit 140 and/or control module 170) to detect docking port 370, determine the relative position and/or orientation of docking arm 330 to docking port 370, and/or the like. In some examples, imaging device 380 may be a 2D imaging device capturing 2D images of access port 340 and/or docking port 370. In some examples, the shape, the orientation, and/or indicia of docking port 370 in the one or more images may be used to detect docking port 370 and/or the relative orientation of docking arm 330 to docking port 370. In some examples, a relative distance between docking arm 330 and docking port 370 may be determined based on a relative size of docking port 370 in the one or more images. In some examples, the relative distance between docking arm 330 and docking port 370 may alternatively be determined using a ranging unit mounted near a distal end of docking arm 330 and/or mounting linkage 320. In some examples, the ranging unit may be an ultrasonic ranging unit, an infrared ranging unit, and/or the like. In some examples, imaging device 380 may be a 3D imaging device whose images may be analyzed to determine the relative position and/or orientation of docking arm 330 to docking port 370 as well as the relative distance between docking arm 330 and docking port 370.

As shown in FIG. 3B, the one or more docking support mechanisms include a registration mechanism 390 mounted to docking arm 330 and docking port 370. And although registration mechanism 390 is shown mounted on docking arm 330, registration mechanism 390 may be mounted at other locations, such as near the distal end of mounting linkage 320. Registration mechanism 390 may alternatively mounted to other locations on docking port 370 and/or access port 340. A shape of registration mechanism 390 may be used to determine the relative position and/or orientation of docking arm 330 to docking port 370. In some examples, the mounting of registration mechanism 390 to both docking arm 330 and docking port 370 may be used to detect docking port 370. In some examples, computer-assisted device 310 and/or a computer-assisted system coupled with computer-assisted device 310 (e.g., control unit 140 and/or control module 170) may communicate with registration mechanism 390 to query one or more sensors and/or a shape reporting unit to determine the shape of registration mechanism 390 and, thus, the relative position and/or orientation of docking arm 330 to docking port 370. In some examples, registration mechanism 390 may include an articulated structure whose relative joint positions and/or angles may be used to determine the shape of registration mechanism 390. In some examples, registration mechanism 390 may include a shape sensor. The shape sensor may optionally include an optical fiber along its length that forms a fiber optic bend sensor for determining the shape of registration mechanism 390. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. Patent Application Publication No. 2006/0013523; U.S. Pat. Nos. 7,772,541; and 6,389,187, each of which are incorporated by reference herein.

As discussed above and further emphasized here, FIGS. 3A and 3B are merely examples which should not unduly limit the scope of the claims. One of ordinary skill in the art would recognize many variations, alternatives, and modifications. According to some embodiments, other mechanisms may be used to detect docking port 370 and/or to determine the relative position and orientation of docking arm 330 to docking port 370. In some examples, the other mechanisms may include one or more of sensors to detect one or more fiducial markers on and/or near docking port 370, one or more sensors to detect one or more emitters on and/or near docking port 370, one or more magnetic sensors to detect a magnetic pattern of docking port 370 and/or access port 340, and/or the like. In some examples, combinations of two or more of imaging sensor 380, registration mechanism 390, and/or any of the other mechanisms may be used in combination to detect docking port 370 and/or to determine the relative position and orientation of docking arm 330 to docking port 370.

In some embodiments, one or more sensing mechanisms may be mounted at or near the distal end of mounting arm 320 in order to detect docking between docking arm 330 and docking port 370. The one or more sensors may include one or more contact sensors, one or more magnetic sensors, one or more sensors detecting one or more emitters on and/or near docking port 370, and/or the like.

In some embodiments, docking arm 330 and/or mounting linkage 320 may further include an inertial measurement unit. In some examples, the inertial measurement unit may be used to supplement the sensing and/or detecting mechanisms, such as when the sensing and/or detecting mechanisms are not able to provide an update on the relative position and/or orientation of docking arm 330 to docking port 370 with sufficient frequency.

Figure 4:
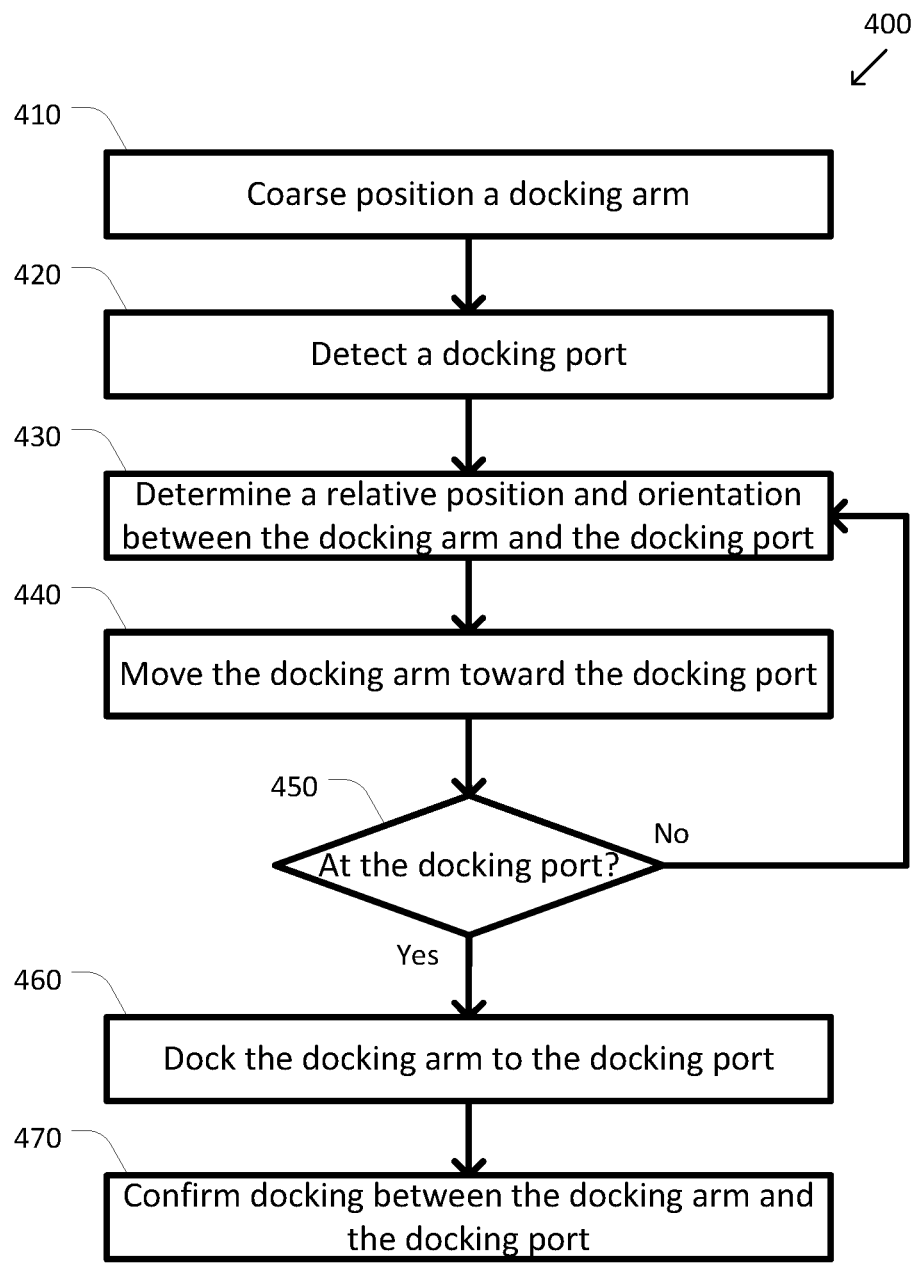
FIG. 4 is a simplified diagram of a method of docking a computer-assisted device to a docking port according to some embodiments.

FIG. 4 is a simplified diagram of a method 400 of docking a computer-assisted device to a docking port according to some embodiments. One or more of the processes 410-470470 of method 400 may be implemented, at least in part, in the form of executable code stored on non-transitory, tangible, machine readable media that when run by one or more processors (e.g., the processor 150 in control unit 140) may cause the one or more processors to perform one or more of the processes 410-470470. In some embodiments, method 400 may be performed by one or more modules, such as control module 170. In some embodiments, method 400 may be used to automatically and/or semi-automatically dock a docking arm (e.g., docking arm 270 and/or 330) of a computer-assisted device (e.g., computer-assisted device 110, 200, and/or 310) to a docking port (e.g., docking port 370). In some embodiments, process 410 is optional and may be omitted.

In some embodiments, method 400 may be performed in a different order than the order implied by FIG. 4. In some examples, processes 410 and 420 may be performed concurrently. In some examples, processes 430-460 may be performed concurrently. In some examples, process 470 may occur concurrently with process 460 so that the docking of process 460 occurs until docking is confirmed using process 470.

At an optional process 410, coarse positioning of a docking arm is performed. In some examples, the docking arm may be consistent with docking arm 270 and/or 330. In some examples, the coarse positioning of the docking arm may position and/or orient the docking arm so that it is within a threshold distance of the docking port and/or oriented toward the docking port so that docking arm is within a threshold angle of being aligned with the docking port. In some examples, the coarse positioning of the docking arm may include positioning the docking arm close enough to the docking port so that a registration mechanism, such as registration mechanism 390 may be mounted between the docking arm and the docking port. In some examples, the course positioning of the docking arm may include positioning and/or orienting the docking arm so that an imaging device, such as imaging device 380, is able to capture images of the docking port that are usable to detect the docketing port. In some examples, the coarse positioning of the docking arm may include positioning and/or orienting the docking arm so that one or more sensors of the docking arm and/or the computer-assisted device are able to detect the docking port.

In some examples, the coarse positioning of the docking arm may be performed by an operator by teleoperating the computer-assisted device, placing the computer-assisted device in a clutching mode and applying manual repositioning of the docking arm, and/or the like. In some examples, the computer-assisted device may be placed in the clutching mode by activating one or more buttons on the computer-assisted device, the mounting linkage, and/or the mounting arm, one or more operator controls on a console, and/or the like.

In some examples, the computer-assisted device may indicate that the coarse positioning is sufficient by notifying the operator with an alert. In some examples, the alert may include one or more of an audible beep, an informational message on a display screen, illumination of one or more indicators, a haptic response (e.g., a vibration), and/or the like. In some examples, the coarse positioning is sufficient when successful mounting of the registration mechanism is detected, the imaging device and/or one or more sensors are able to detect the docking port, and/or the like.

At a process 420, the docking port is detected. In some examples, the docking port may be detected by detecting successful mounting of a registration mechanism (e.g., registration mechanism 390) to both the docking arm and the docking port. In some examples, the docking port may be detected by analyzing one or more images captured by an imaging device (e.g., imaging device 380) to detect a shape and/or pattern of the docking port and/or the access port, one or more indicia and/or fiducial markers on and/or near the docking port, and/or the like. In some examples, the docking port may be detected using one or more sensors to detect the one or more indicia and/or fiducial markers, one or more emitters on and/or near the docking port, a magnetic pattern of the docking port and/or the access port, and/or the like. In some examples, combinations of two or more of these approaches may be used to detect the docking port. When the docking port is detected, the operator may be notified using an alert as previously described and/or method 400 may continue using a process 430. When the docking port is not detected, further positioning and/or orientation of the docking arm may be used, such as by returning to process 410, until the docking port is detected.

At a process 430, a relative position and/or orientation between the docking arm and the docking port is determined. In some examples, determining the relative position and/or orientation between the docking arm and docking port may include determining one or more of a direction of an alignment point of the docking port relative to the docking arm, an orientation of an alignment axis of the docking arm relative to an alignment axis of the docking port, a relative orientation of the docking arm about the alignment axis of the docking port, a relative distance between the docking arm and the docking port, and/or the like. In some examples, the relative position and/or orientation between the docking arm and the docking port may be determined using the registration mechanism, analyzing one or more images obtained by the imaging device, analyzing information from one or more sensors, and/or the like such as discussed above with respect to the embodiments of FIGS. 3A and 3B and/or other embodiments.

At a process 440, the docking arm is moved toward the docking port. In some examples, the movement may include aligning the docking arm with the docking port and reducing the relative distance between the docking arm and the docking port until docking occurs. Numerous strategies may be used to perform the aligning, relative distance reducing, and/or docketing, such as is described in method 500 of FIG. 5 as described below. In some examples, the docking may be performed based on the relative position and orientation between the docking arm and the docking port determined during process 430. In some examples, the docking may be performed by actuating one or more actuators to control one or more joints in the computer-assisted device, the mounting linkage, and/or the docking arm. In some examples, the actuating may include sending one or more signals (e.g., voltages, currents, pulse-width modulated signals, and/or the like) to the one or more actuators. In some examples, the actuating may include using the relative position and/or orientation between the mounting arm and the mounting port along with one or more kinematic models of the computer-assisted device, the mounting linkage, and/or the mounting arm to determine the motion of the computer-assisted device, the mounting linkage, and/or the mounting arm to be performed to achieve the docking. In some examples, the relative position and/or orientation between the docking arm and the docking port may be updated during process 440 using an inertial measurement unit.

Figure 5:
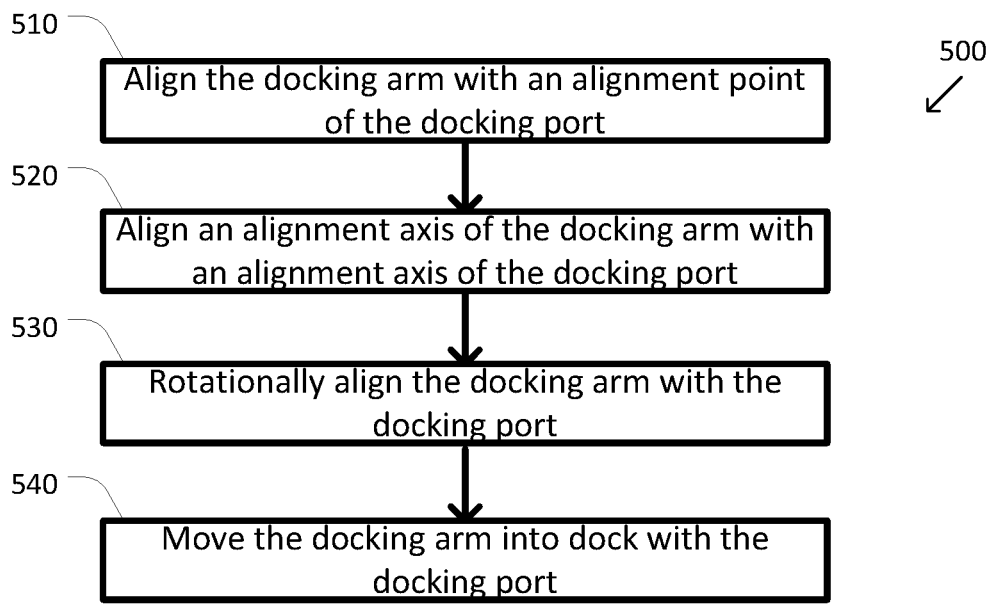
FIG. 5 is a simplified diagram of a moving a computer-assisted device toward a docking port according to some embodiments.

FIG. 5 is a simplified diagram of a method 500 of moving a computer-assisted device toward a docking port according to some embodiments. In some embodiments, method 500 may be used to perform process 460. One or more of the processes 510-540 of method 500 may be implemented, at least in part, in the form of executable code stored on non-transitory, tangible, machine readable media that when run by one or more processors (e.g., the processor 150 in control unit 140) may cause the one or more processors to perform one or more of the processes 510-540. In some embodiments, method 400 may be performed by one or more modules, such as control module 170. In some embodiments, method 500 may be used to align a docking arm with a docking port and/or move the docking arm into docking position with the docking port. In some embodiments, method 500 may be performed in a different order than the order implied by FIG. 5. In some examples, processes 510-530 may be performed in any order and/or concurrently. In some examples, process 540 may be performed concurrently with processes 510-530 as long as suitable alignment is obtained before the actual docking occurs.

Method 500 is further described with respect to FIGS. 6A-6D, which are simplified diagrams showing various stages of docking according to some embodiments. However, it is understood that FIGS. 6A-6D are representative only as the docking may begin with different relative positions and/or orientations between the docking arm and the docking port and/or may the alignment between the docking arm and the docking port may occur in different orders. As shown in FIGS. 6A-6D, the stages of docking to a docking port 610 or an access port 600 are shown from the perspective of the docking arm, such as might be seen by the one or more images obtained from the imaging device of the docking arm. To aid in depiction of the relative position and orientation between the docking arm and the docking port, a center point of the one or more images, which corresponds to a direction of the alignment axis of the docking arm is depicted using cross-hairs 640. In some examples, cross-hairs 640 may optionally be superimposed on the one or more images when the one or more images are displayed to an operator.

Figure 6A:
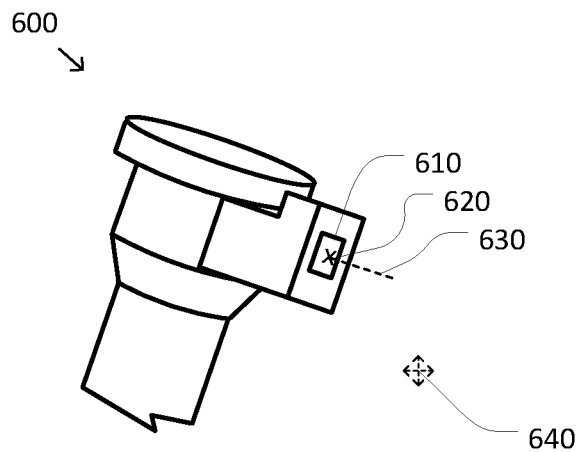
FIGS. 6A-6D are simplified diagrams showing various stages of docking according to some embodiments.
Figure 6B:
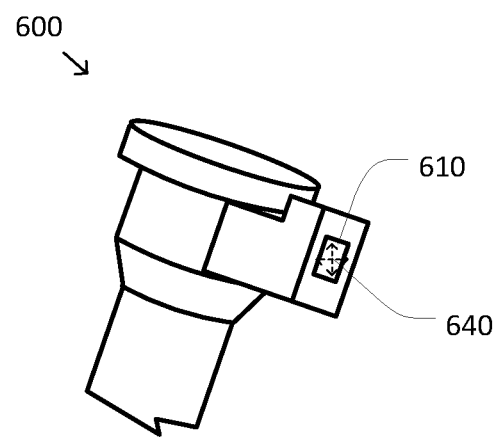

At a process 510, the docking arm is aligned with an alignment point 620 on the docking port 610. In some examples, an alignment point 620 on docking port 610 may correspond to a center point of docking port 610. In some examples, alignment point 620 on docking port 610 may correspond with an alignment axis 630 of docking port 610 that is to be aligned with an alignment axis of the docking arm before docking may complete. FIG. 6A shows the relative position and/or orientation between the docking arm and docking port 610 in the early stages of docking (e.g., before and/or during process 510) where the docking arm is not aligned with alignment point 620 of docking port 610, such as is shown because cross-hairs 640 are not aligned over alignment point 620 of docking port 610. FIG. 6B shows the relative position and/or orientation between the docking arm and docking port 610 after completion of process 510, such as is shown because cross-hairs 640 are aligned with alignment point 620 of docking port 610. Note, alignment point 620 and alignment axis 630 are not depicted in FIGS. 6B-6D to avoid clutter in the figures.

Figure 6C:
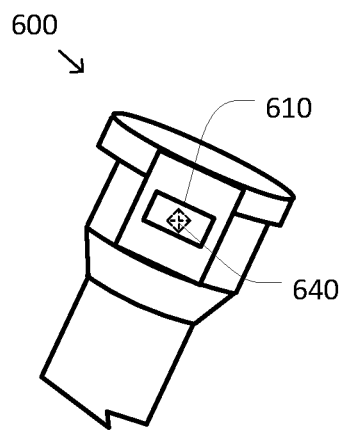

At a process 520, the alignment axis of the docking arm is aligned with alignment axis 630 of docking port 610. In some examples, aligning the alignment axis of the docking arm with alignment axis 630 of docking port 610 includes rotating the docking arm about docking port 610 (e.g., about alignment point 620 of docking port 610) so that the alignment axis of the docking arm is coincident with alignment axis 630. FIG. 6C shows the relative position and/or orientation between the docking arm and docking port 610 after completion of process 520, such as is shown because cross-hairs 640 are aligned with alignment point 620 of docking port 610 and the docking arm is oriented to face toward docking port 610 so that a docking feature of the docking arm is able to move straight into docking port 610.

Figure 6D:
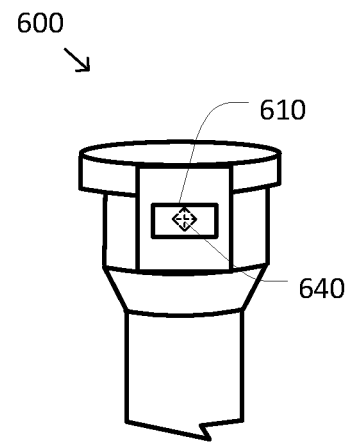

At a process 530, the docking arm is rotationally aligned with docking port 610. In some examples, rotationally aligning the alignment axis of the docking arm with docking port 610 includes rotating the docking arm about the alignment axis of the docking arm so that an orientation of the docking feature of the docking arm is aligned to correctly mate with docking port 610. In some examples, process 530 helps ensure that when docking port 610 is keyed (e.g., as shown in FIGS. 6A-6D due to the rectangular shape of docking port 610) that the docking arm may only dock with docking port 610 when the docking feature and docking port 610 are correctly oriented with respect to each other. FIG. 6D shows the relative position and/or orientation between the docking arm and docking port 610 after completion of process 530, such as is shown because cross-hairs 640 are aligned with alignment point 620 of docking port 610, the docking arm is oriented to face toward docking port 610, and the docking feature of the docking arm is oriented with a same orientation as docking port 610.

At a process 540, the docking arm is moved into dock with docking port 610. In some examples, the docking arm is moved into dock with docking port 610 by reducing the relative distance between the docking arm and docking port 610 by moving the docking arm closer to docking port 610. In some examples, the docking arm may be moved toward docking port 610 at a constant speed and/or at a speed that is reduced as the relative distance between the docking arm and docking port 610 shortens. Process 540 continues until the relative distance is determined to be zero and/or docking is detected (e.g., using process 470 as is described further below).

As discussed above and further emphasized here, FIGS. 5 and 6A-6D are merely examples which should not unduly limit the scope of the claims. One of ordinary skill in the art would recognize many variations, alternatives, and modifications. According to some embodiments, other shapes and/or arrangements are possible for docking port 610. In some examples the shape of docking port 610 may be an oval. In some examples, docking port 610 may be keyed with a shape that allows the rotational aligning of process 530 to occur at more than the two angles allowed by the rectangular shape of docking port 610. In some examples, the possible shapes include an equilateral triangle, a square, a pentagon, a hexagon, a star shape, and/or the like. In some examples, docking port 610 may be keyed with a shape that allows the rotational aligning of process 530 to occur at only a single angle. In some examples, the possible shapes include a trapezoid, a D shape, and/or the like. In some examples, docking port 610 may not be keyed (e.g., with a circular shape). In some examples, when docking port 610 is not keyed, process 530 may be performed after process 540 because the docking arm may be rotationally aligned with docking port 610 after docking during process 540.

Referring back to FIG. 4, at a process 450, it is determined whether the docking arm is at the docking port. In some examples, whether the docking arm is at the docking port may be determined based on the one or more kinematic models and/or information for the inertial measurement unit. In some examples, whether the docking arm is at the docking port may be determined using one or more sensors on the docking arm and/or the mounting linkage that are able to detect correct alignment and positioning between the docking arm and the docking port. In some examples, the one or more sensors may detect a magnetic pattern of the docking port, depression of and/or pressure on one or portions of the docking arm by the docking port, and/or the like. In some examples, the docking port is determined to be at the docking are when successful completion of process 540 is detected. When it is determined that the docking arm is not at the docking port, processes 430-450 may be repeated until the docking arm is at the docking port. When it is determined that the docking arm is at the docking port, the docking arm is docked to the docking port using a process 460.

At a process 460, the docking arm is docked at the docking port. In some examples, the docking arm may be docked at the docking port by automatic engagement of one or more latching mechanisms (e.g., one or more levers, pins, and/or the like) between the docking arm and the docking port, and/or the like. In some examples, the docking arm may be docked at the docking port by an operator manually engaging one or more latching mechanisms (e.g., one or more levers, pins, and/or the like) between the docking arm and the docking port.

At a process 470, docking between the docking arm and the docking port is confirmed. In some examples, docking between the docking arm and the docking port may be confirmed by the one or more sensors on the docking arm and/or the mounting linkage that are able to detect correct alignment and positioning between the docking arm and the docking port. In some examples, the one or more sensors may detect a magnetic pattern of the docking port, depression of and/or pressure on one or portions of the docking arm by the docking port, the engagement of the one or more latching mechanisms between the docking arm and the docking port, and/or the like. In some examples, docking between the docking arm and the docking port may be confirmed by the operator manually engaging the one or more latching mechanisms (e.g., one or more levers, pins, and/or the like) between the docking arm and the docking port, activating one or more controls (e.g., a button on the docking arm, the mounting linkage, at an operator workstation, and/or the like), issuing a voice confirmation command, and/or the like.

In some examples, the computer-assisted device may indicate that the docking is confirmed by notifying the operator with an alert. In some examples, the alert may include one or more of an audible beep, an informational message on a display screen, illumination of one or more indicators, a haptic response (e.g., a vibration), and/or the like.

As discussed above and further emphasized here, FIG. 4 is merely an example which should not unduly limit the scope of the claims. One of ordinary skill in the art would recognize many variations, alternatives, and modifications. According to some embodiments, method 400 may be prematurely terminated by an operator. In some examples, the operator may prematurely terminate method 400 by activating an input control (e.g., a button) on the docking arm, the mounting linkage, at an operator workstation and/or the like. In some examples, the operator may prematurely terminate method 400 by pushing against the docking arm and/or the mounting linkage with sufficient force. In some examples, the pushing may be detected due to an inability of the computer-assisted device to complete the docking (e.g., by detecting one or more position and/or orientation errors in the docking arm above a corresponding threshold, by detecting an inability to complete a desired docking motion (e.g., during any of processes 440-460 and/or 510-540) without exceeding a corresponding force and/or torque threshold associated with one or more of the actuators of the computer-assisted device, the mounting linkage, the mounting arm, and/or the like. In some examples, the one or more position and/or orientation errors and/or the one or forces and/or torques above a corresponding threshold may also be caused by one or more obstacles, a collision, and/or improper alignment with the docking port.

In some embodiments, method 400 and/or process 470 may include further safe guards. In some examples, as docking is detected during process 470, process 470 may further make a determination whether the docking port is a correct docking port. In some examples, one or more sensors may be used to detect an error in a magnetic pattern of the docking port, incorrect indicia on the docking port, and/or the like. In some examples, the computer-assisted device may access a processor, a chip, a memory device, and/or the like on the docking port and/or the access port to determine whether a type of the docking port and/or the access port and/or an identifier (e.g., a serial number, access port number, and/or the like) is correct.

Some examples of control units, such as control unit 140 may include non-transitory, tangible, machine readable media that include executable code that when run by one or more processors (e.g., processor 150) may cause the one or more processors to perform the processes of methods 400 and/or 500. Some common forms of machine readable media that may include the processes of methods 400 and/or 500 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
    a linkage;
    a docking arm located near a distal end of the linkage;
    a docking support mechanism; and
    one or more processors coupled to the linkage and the docking support mechanism;
    wherein the one or more processors are configured to:
        detect a docking port of an access port using the docking support mechanism; and
        actuate the linkage based on the detection to:
            align the docking arm with an alignment point of the docking port;
            align an alignment axis of the docking arm with an alignment axis of the docking port, wherein the alignment axis of the docking port is different than a direction through which an instrument is inserted through the access port;
            rotate the docking arm about the alignment axis of the docking port; and
            dock the docking arm to the docking port.

2. The computer-assisted device of claim 1, wherein the alignment axis of the docking port is perpendicular to the direction through which an instrument is inserted through the access port.

3. The computer-assisted device of claim 2, wherein a workspace accessed by the instrument through the access port is associated with an interior anatomy of a patient.

4. The computer-assisted device of claim 1, wherein the docking port is keyed with a shape to enforce rotational alignment between the docking support mechanism and the docking arm when the docking arm is docked to the docking port.

5. The computer-assisted device of claim 1, wherein the docking support mechanism includes an imaging device.

6. The computer-assisted device of claim 1, wherein the docking support mechanism includes a registration mechanism configured to be mounted to both the docking port and one of the docking arm or the linkage.

7. The computer-assisted device of claim 6, wherein the registration mechanism comprises at least one of an articulated structure or a shape sensor.

8. The computer-assisted device of claim 1, wherein the docking support mechanism includes an inertial measurement unit.

9. The computer-assisted device of claim 1, wherein to actuate the linkage based on the detection, the one or more processors are configured to reduce a relative distance between the docking arm and the docking port.

10. The computer-assisted device of claim 1, wherein the alignment point of the docking port is a center point of the docking port.

11. The computer-assisted device of claim 1, wherein to align the alignment axis of the docking arm with the alignment axis of the docking port, the one or more processors are configured to make the alignment axis of the docking arm and the alignment axis of the docking port coincident.

12. The computer-assisted device of claim 1, wherein the one or more processors are further configured to detect docking of the docking arm to the docking port.

13. A method comprising:
  detecting, by one or more processors, a docking port of an access port using a docking support mechanism; and
  actuating, by the one or more processors, a linkage of a docking arm of a computer-assisted device based on the detecting, wherein the actuating comprises:
    aligning the docking arm with an alignment port of the docking port;
    aligning an alignment axis of the docking arm with an alignment axis of the docking port, wherein the alignment axis of the docking port is different than a direction through which an instrument is inserted through the access port;
    rotating the docking arm about the alignment axis of the docking port;
    moving the docking arm toward the docking port; and
    docking the docking arm with the docking port.

14. The method of claim 13, wherein the alignment axis of the docking port is perpendicular to the direction through which an instrument is inserted through the access port.

15. The method of claim 13, wherein the docking port is keyed with a shape to enforce rotational alignment between the docking support mechanism and the docking arm when the docking arm is docked to the docking port.

16. The method of claim 13, wherein the docking support mechanism includes an imaging device.

17. The method of claim 13, wherein:
  the docking support mechanism includes a registration mechanism configured to be mounted to both the docking port and one of the docking arm or the linkage; and
  the registration mechanisms comprises at least one of an articulated structure or a shape sensor.

18. The method of claim 13, wherein actuating the linkage based on the detecting, comprises reducing a relative distance between the docking arm and the docking port.

19. The method of claim 13, further comprising coarse positioning the docking arm near the docking port, wherein the coarse positioning of the docking arm near the docking port comprises one or more of:
  moving the docking arm within a threshold distance of the docking port; or
  aligning the docking arm within a threshold angle of the alignment axis of the docking port; or
  teleoperating the docking arm or the linkage; or
  manually positioning the docking arm using a clutching mode.

20. The computer-assisted device of claim 1, wherein the one or more processors are further configured to, upon rotating the docking arm about the alignment axis of the docking port, move the docking arm toward the docking port.

* * * * *